United States Patent
Solazzo

Patent Number: 5,531,723
Date of Patent: Jul. 2, 1996

[54] URETERAL CATHETER CONNECTOR ADAPTER

[76] Inventor: Anthony Solazzo, 904 Oak Tree Rd., South Plainfield, N.J. 07080

[21] Appl. No.: 230,099

[22] Filed: Apr. 20, 1994

[51] Int. Cl.$^6$ .................................................. A61M 25/00
[52] U.S. Cl. ...................... 604/283; 604/43; 604/158; 604/905
[58] Field of Search .................................. 604/43, 82, 83, 604/158, 167, 283, 284, 905, 327, 328

[56] References Cited

U.S. PATENT DOCUMENTS

| | | | |
|---|---|---|---|
| 3,144,868 | 8/1964 | Jascalevich | 604/43 |
| 4,072,146 | 2/1978 | Howes | 604/158 |
| 4,601,701 | 7/1986 | Mueller, Jr. | 604/83 |
| 4,737,145 | 4/1988 | Sharrow | 604/83 |
| 4,846,405 | 7/1989 | Zimmerman | 604/83 |
| 5,207,661 | 5/1993 | Repschlager | 604/327 |
| 5,300,022 | 4/1994 | Klapper et al. | 604/43 |
| 5,358,490 | 10/1994 | Henry et al. | |

Primary Examiner—John D. Yasko
Assistant Examiner—Laird J. Knights
Attorney, Agent, or Firm—Kenneth P. Glynn

[57] ABSTRACT

The present invention is a ureteral catheter-foley catheter connector adapter for connecting ureteral catheters to a foley catheter-foley collection bag arrangement. It includes a main body having a top and a bottom and a first hollow orifice located therein with an inlet at the top and an outlet at the bottom of the main body. The main body has at least one shoulder extending outwardly therefrom, and each shoulder has at least one orifice therein forming a shoulder inlet. The shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms. The present invention is also directed to a system which includes at least one ureteral catheter, a foley catheter, a foley collection bag and the connector adapter.

8 Claims, 3 Drawing Sheets

URETERAL CATHETER CONNECTOR ADAPTER

BACKGROUND OF THE INVENTION

1. Field of the Invention

The present invention is directed to a connector adapter for interconnecting a foley catheter or other type of catheter with ureteral catheters so that they may drain into the same drainage bag. More specifically, the present invention involves an adapter which has shoulders with inlets for ureteral catheters which have means for connecting the ureteral catheters to the adapter.

2. Information Disclosure Statement

Various catheter connectors have been developed and the following prior art is representative of the state of the art:

U.S. Pat. No. 4,337,775 is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

U.S. Pat. No. 4,385,631 is directed to a system which includes at least one ureteral ureteral catheter-foley catheter connector catheter, a foley catheter, a foley collection adapter for connecting ureteral bag and the connector adapter. catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

U.S. Pat. No. 4,661,110 is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

U.S. Pat. No. 5,100,395 is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

U.S. Pat. No. 5,163,902 is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

U.S. Pat. No. 5,176,637 is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

Notwithstanding the formidable prior art, there is no device or system which suggests or renders obvious the present invention.

SUMMARY OF THE INVENTION

The present invention is directed to a ureteral catheter-foley catheter connector adapter for connecting ureteral catheters to a foley catheter-foley collection bag arrangement. It includes a main body having a top and a bottom and having a first hollow orifice located therein with an inlet at the top of the main body and an outlet at the bottom of the main body. The main body has at least one shoulder extending outwardly therefrom, and each shoulder has at least one orifice therein forming a shoulder inlet. Each of the shoulder orifices are connected to the first hollow orifice of the main body. The shoulder inlets include connecting mechanisms for fixedly connecting the shoulder inlets to ureteral catheters. These may be tapered walls for force-fitting the ureteral catheter distal ends, O-ring fittings, flexible neck portions of the shoulder inlets or other mechanisms.

The present invention is also directed to a system which includes at least one ureteral catheter, a foley catheter, a foley collection bag and the connector adapter.

BRIEF DESCRIPTION OF THE DRAWINGS

The present invention is more fully understood when the present specification is taken in conjunction with the drawings appended hereto, wherein.

DETAILED DESCRIPTION OF THE PRESENT INVENTION

During the course of various intraoperative procedures, the urologist may be called upon to assist general surgeons or other specialists for the placement of ureteral catheters in the ureters for their easier identification during difficult abdominal or pelvic surgery. Once these are in place, a foley catheter is inserted into the bladder for fixation of the ureteral catheters so that they do not migrate out. These can be placed in separate urinary collection devices, or, more commonly, may be placed through the foley catheter wall slightly above its connection to the foley bag tubing. This is usually done by perforating the foley catheter wall at its neck with a number 14 or number 16 needle and sheath. The ureteral catheter is guided through the sheath and together are pulled through the lumen of the foley catheter. This can be time consuming and an inadvertent puncture from the needles is always a possibility. Additionally, there is frequent leakage around the puncture sights.

In response to the aforesaid problems, the present invention ureteral catheter connector adapter has been developed so as to be a simple device which is interposed between the foley and the foley bag tubing connector. Its general shape consists of a firm, male tapered connector at the proximal end for connection to the foley catheter female and/or distal end and a softer, funnel-like distal end to adapt to connection with the foley bag tubing connector. In the central portion or main body of the present invention connector adapter, there is at least one shoulder upon which there are orifices which may take the form of inverted nipples for the insertion of the ureteral catheter ends. By this technique, retention is assured by using thicker wall and narrow lumen at the insertion end of the nipple. Leak resistance is more a result of the thinner elastic walled distal end is some embodiments. The ureteral catheter connector adapter of the present invention is a unique device which can simplify ureteral catheter connections to the foley bag tubing, offering safety and the economy of intraoperative time.

A critical feature of the present invention connector adapters is the need for means of connecting the ureteral catheters to the adapter connectors and these means or mechanisms may take the form of O-rings, tapered inlets, flexible inverted nipples, graded diameter ridges or otherwise.

Figure 1:
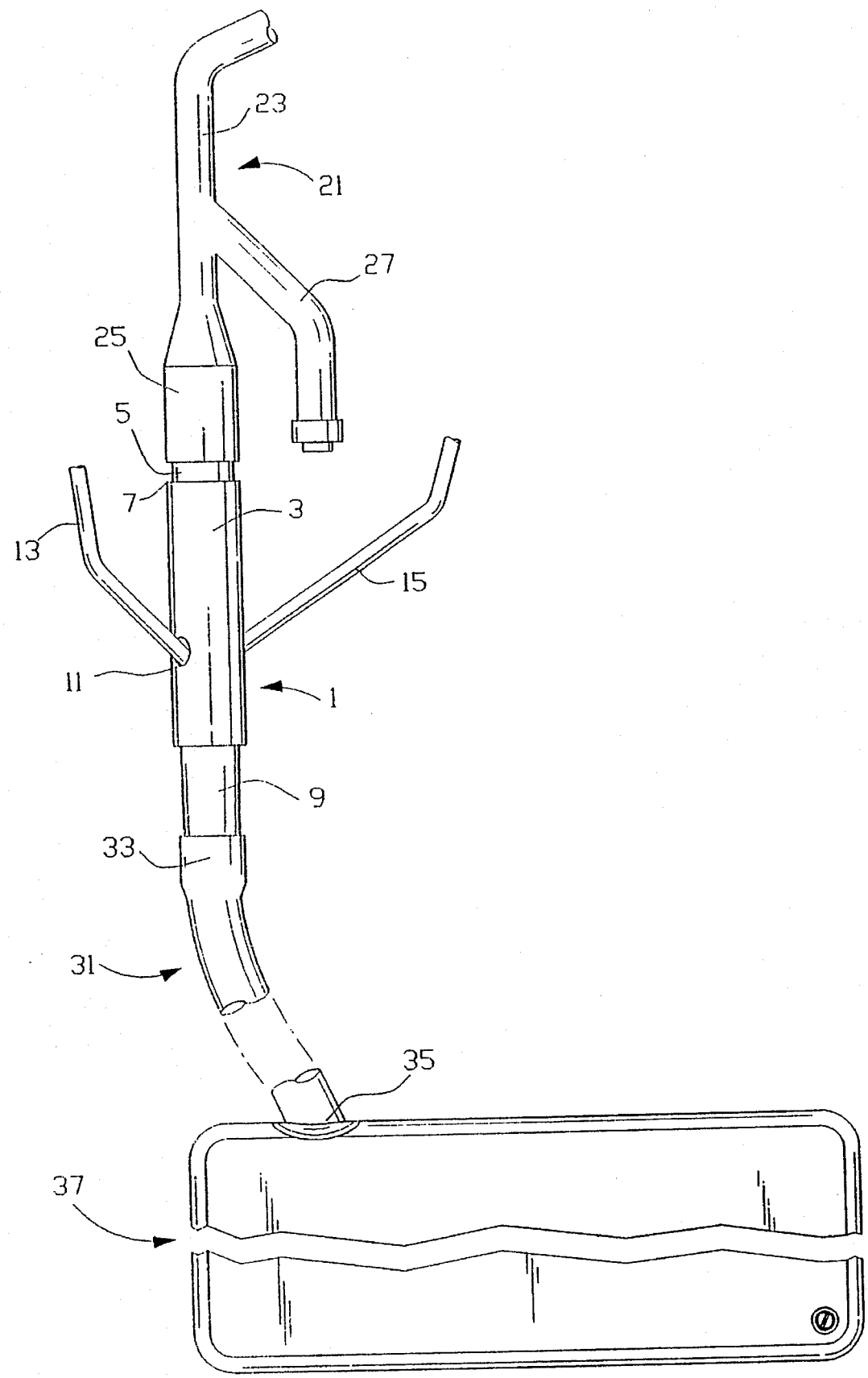
FIG. 1 shows a front view of a complete present invention system including two ureteral catheters, a foley catheter, a present invention adapter and a drainage bag.

Referring now to FIG. 1, there is shown a front view of a ureteral catheter-foley catheter-connector adapter-system of the present invention. This includes adapter 1, foley catheter 21, drainage bag connection tubing 31 and drainage bag 37. More specifically, connector adapter 1 includes a main body 3 as well as an inlet 5 and an outlet 9. Shoulder 7 includes two orifices forming Shoulder inlets such as shoulder inlet 11. Each of these shoulder inlets connect to a first hollow orifice (not shown) of main body 3. Foley catheter 21 includes a main line section 23 which is shown in part and may connect to a balloon and has an access port connected to elbow 27. Distal end 25 of foley catheter 21 is connected to inlet 5 as shown. Ureteral catheters 13 and 15 are connected to the shoulder orifices such as shoulder orifice 11 and another shoulder orifice opposite thereof (not shown). At the bottom of main body 3, at outlet 9, drainage bag 37 has a tube 31 which is connected to outlet 9 at tube end 33 and connected at opposite tube end 35 to drainage bag 37.

Figure 2:
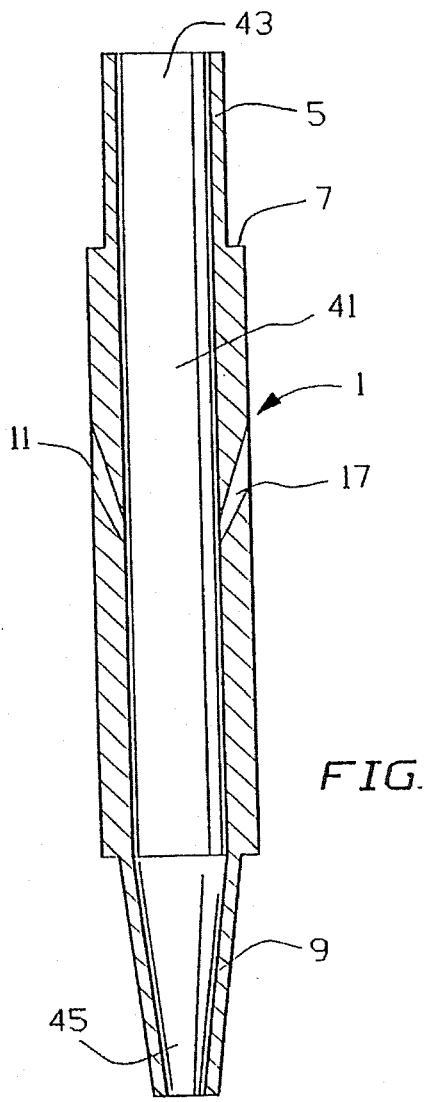
FIG. 2 shows a front cut view of the connector adapter shown as part of the system in FIG. 1.

FIG. 2 shows a front cut view of connector adapter 1 shown in FIG. 1. Identical parts are identically numbered. Note that there is a first hollow orifice 41 which extends from opening 43 at inlet 5 all the way down to opening 45 at outlet 9. Note that shoulder orifices 11 and 17 are shown to be tapered to enable ureteral catheters to be force-fitted therein and to enable that device to receive ureteral catheters of different size diameters. Note that all parts identical to those shown in FIG. 1 are identically numbered in FIG. 2.

Figure 3:
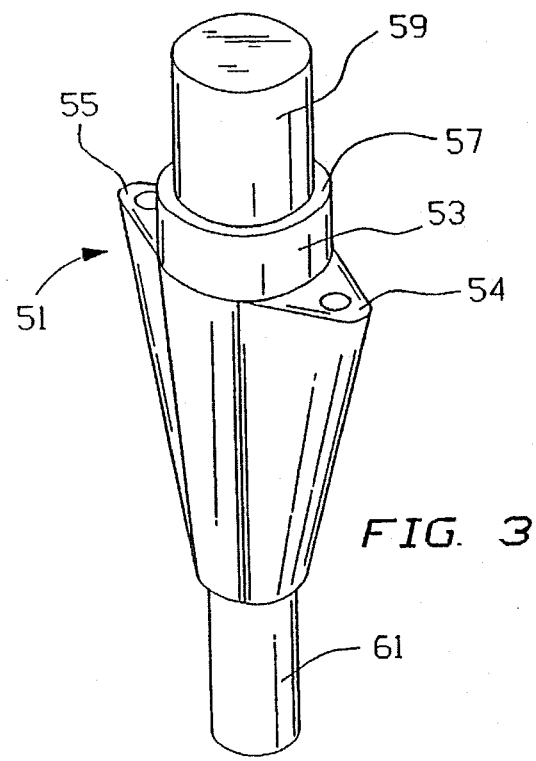
FIGS. 3, 4 and 5 show an oblique view, a cut front view and a partial blown-up cut front view of an alternative present invention connector adapter device.
Figure 4:
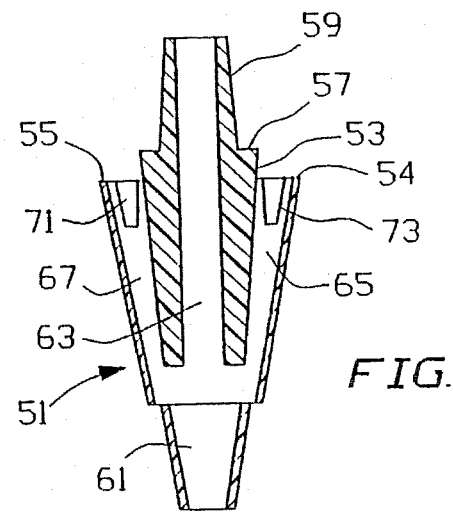
Figure 5:
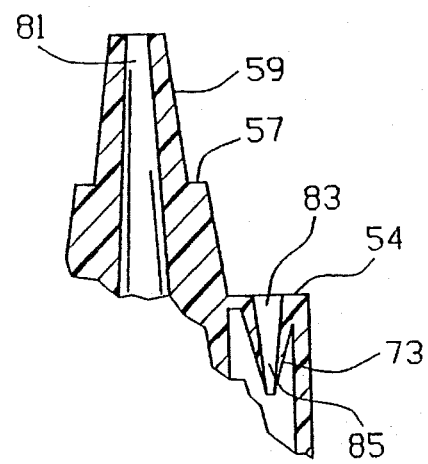

FIGS. 3, 4 and 5 collectively show an oblique view, a front cut view, and a partial cut blown-up view of present invention connector adapter 51. Here there is a shoulder 57 as well as additional shoulders 54 and 55 formed as part of main body 53 with inlet 59 and outlet 61. In FIG. 4 there is shown an inverted nipple 71 at shoulder 55 and an inverted nipple 73 at shoulder 54. These are flexible and tapered and are illustrated by the blow-up of the right side of FIG. 4 shown in FIG. 5. FIG. 4 shows a first hollow orifice 63 extending from inlet 59 to outlet 61 with second and third hollow orifices 65 and 67 which respectively extend from inverted nipples 71 and 73 respectively.

As shown in FIG. 5, the inlet 59 has opening 81 for fluids from the foley catheter to drain down into it. Shoulder 54 with flexible nipple 73 has an orifice 83 with an internal outlet 85 for drainage into second hollow orifice 65 as shown in FIG. 4. By the walls of inverted nipple 73 being flexible and stretchable, a ureteral catheter can be easily pushed in but not so easily removed from inverted nipple 73 and this will secure the ureteral catheter to avoid both leakage and inadvertent removal during surgery.

Figure 6:
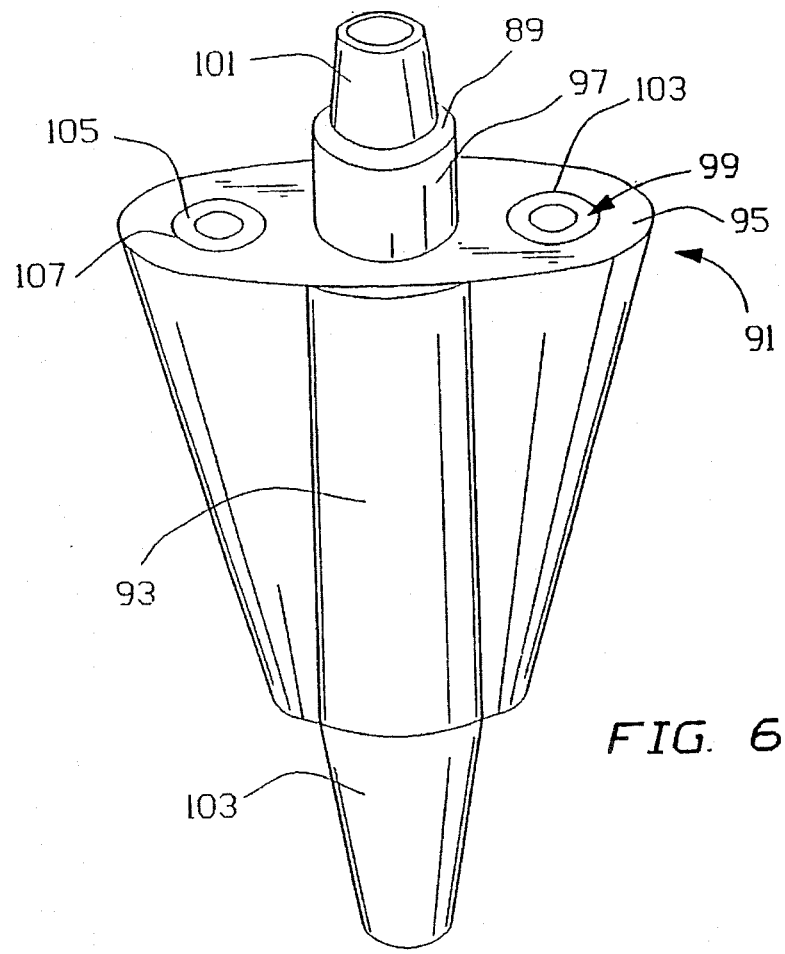
FIG. 6 shows a front view of yet another present invention connector adapter device; and, FIG. 7 shows a partial cut front view of one shoulder of a present invention connector adapter device illustrating the connecting means for ureteral catheters.

FIG. 6 shows yet another embodiment of the present invention connector adapters, here adapter 91 includes a main body 93 with a collar 97 and shoulder 89 and a second shoulder 95. This includes two shoulder orifices such as shoulder orifice 103 which contains O-ring fitting 99 for grasping an inserted ureteral catheter. Likewise, O-ring 105 at shoulder orifice 107 will function similarly. The O-ring fittings 99 and 105 may be torroidal rubber-like insertions which both aid to secure inserted ureteral catheters as well as to minimize leakage. Outlet 103 would be connected to tubing to a drainage bag as desired.

Figure 7:
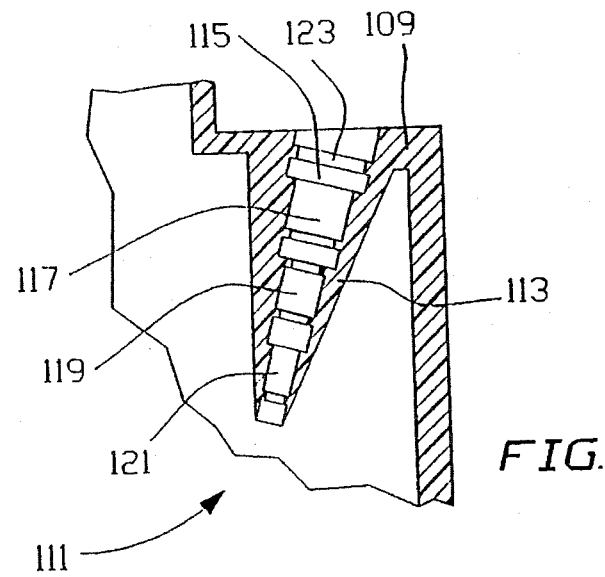

FIG. 7 shows a partial front cut view of one shoulder 109 of a present invention adapter 111 and has inverted nipple 113 with a variety of step down diameter cuts beginning with largest cut 115 through intermediate cuts 117 and 119 and smallest cut 129. These will be used to secure various sizes of ureteral catheters and will enable adapter 111 to be utilized as a universal device. Note that ridges such as ridge 123 will act to aid in the forced-fitting securement of an inserted ureteral catheter.

Obviously, numerous modifications and variations of the present invention are possible in light of the above teachings. For example, the present invention adapter is generally shown as having a single structure for the main body. However, this may be molded in two or more pieces and permanently assembled without exceeding the scope of the present invention. In fact, in some preferred embodiments, the main body may be made of a two-piece assembly with the upper half, which connects to the foley catheter, being made of hard plastic or rubber and the lower half being made of softer plastic or rubber to accommodate a drainage bag assembly. It is therefore understood that within the scope of the appended claims, the invention may be practiced otherwise than as specifically described herein.

What is claimed is:

1. A ureteral catheter-foley catheter connector adapter, which comprises:

a main body having a top and a bottom and having a first hollow orifice located therein with an inlet at said top of said main body and an outlet at said bottom of said main body, and having at least one shoulder on said main body extending outwardly therefrom, each of said at least one shoulder having an orifice therein and each such orifice forming a shoulder inlet, each of said shoulder orifices being connected to said first hollow orifice of said main body, said shoulder inlets having a series of increasingly reduced diameter sections adapted to receive ureteral catheter distal ends of predetermined different outer diameters.

2. The adapter of claim 1, wherein said main body has two shoulders.

3. The adapter of claim 2, wherein said shoulder inlets include connecting means for fixedly connecting said shoulder inlets to ureteral catheters.

4. The adapter of claim 3, wherein said connecting means are tapered walls for force-fitting said ureteral catheter distal ends.

5. The adapter of claim 3, wherein said connecting means are O-ring fittings located at said shoulder inlets.

6. The adapter of claim 3, wherein said connecting means are flexible neck portions of said shoulder inlets.

7. The adapter of claim 3, wherein said connecting means are a series of increasingly reduced diameter sections adapted to receive ureteral catheter distal ends of predetermined different outer diameters.

8. The ureteral catheter-foley catheter-connector adapter-system, which comprises:

(a) a foley-catheter having a proximal end and a distal end;

(b) at least one ureteral catheter having a proximal end and a distal end;

(c) an adapter having a main body having a top and a bottom and having a first hollow orifice located therein with an inlet at said top of said main body and an outlet at said bottom of said main body, and having at least one shoulder on said main body extending outwardly therefrom, each of said at least one shoulder having an orifice therein and each such orifice forming a shoulder inlet, said shoulder inlets having a series of increasingly reduced diameter sections adapted to receive ureteral catheter distal ends of predetermined different outer diameters, each of said shoulder orifices being connected to said first hollow orifice of said main body; and, (d) a collection device with a connecting tube; wherein the distal end of said foley-catheter is inserted into said inlet of said first hollow orifice of said main body, and said distal end of said at least one ureteral catheter is inserted into at least one of said shoulder orifices, and said connecting tube being connected to said outlet of said adapter.

* * * * *